United States Patent [19]

Heidgen

[11] Patent Number: Plant 6,366

[45] Date of Patent: Nov. 1, 1988

[54] GERANIUM NAMED DUSTER

[76] Inventor: Charles F. Heidgen, 821 Walnut St., Batavia, Ill. 60510

[21] Appl. No.: 782,739

[22] Filed: Oct. 1, 1985

[51] Int. Cl.[4] ..... A01H 5/00

[52] U.S. Cl. ..... Plt./68

[58] Field of Search ..... Plt./68

*Primary Examiner*—Robert E. Bagwill

[57] ABSTRACT

A new and distinct variety of geranium plant, Duster, characterized by its cascading growth habit; its distinctive small, orange, fluffy looking flowers; its continuous blooming habit; its unique dark green, small, notched foliage; and its exceptional heat tolerance.

1 Drawing Sheet

The present discovery, hereinafter referred to by the cultivar name, Duster, relates to a new and distinct geranium plan.

BACKGROUND

Duster is a new and improved variety which has resulted from definite breeding programs and experiments carried on by me in my greenhouses at 821 Walnut Street, Batavia, Ill. Our experiments commenced in March, 1977 and are being carried on continuously. This seedling, 79×068A, resulted from a cross between Red Heart, an unpatented, cascade geranium and *Pelargonium formatosum,* an unpatented, species geranium.

Asexual reproduction of Duster has been accomplished from vegatative cuttings in my greenhouses in Batavia, Ill. Examination of plants so propagated has demonstrated that the combination of characteristics herein disclosed for Duster are firmly fixed and retained through successive generations of asexual reproduction.

SUMMARY

The new and patentable characteristics of Duster reside in its cascading growth habit, its distinctive fluffy looking, orange flowers, its continuous blooming habit, its unique dark green, notched, small foliage and its exceptional heat tolerance.

DESCRIPTION OF DRAWING

The photograph shows the plant and flower of a fully developed geranium of the new variety, Duster.

BOTANIC DESCRIPTION

The Plant

Growth: Duster is a slightly upright, but cascading geranium with a procumbent growth habit. It is a continuous bloomer and has a small, fluffy-looking, orange flower that is resistant to shattering. The growth rate is rapid, producing a typical 10″ flowering basket in 10–12 weeks from four 2¼ inch plants using standard commercial culture.

Blooming habit: Duster is a very prolific bloomer and very hot weather tolerant. It almost requires long, hot days for optimum blooming performance. Not a very outstanding winter bloomer.

Inflorescence: small-sized head, a roundish, fluffy shape, 1⅔–3 inches in diameter.

Foliage:

*Quantity.*—Abundant.

*Size.*—Small, notched, 1¾–2 inches across.

*Color.*—Spinach Green(0960) with an Ivy Green(0001060/2) zone. (The Royal Horticultural Society Horticultural Colour Chart)

*Texture.*—Waxy, almost wavy.

Stem: Slender, short internodes, cascading habit, slightly upright, free branching.

Petiole: Short, 1–1¼ inches, same color as foliage.

The Flower

Truss:

*Size.*—Small-sized, 1⅔–3 inches in diameter.

*Shape.*—A fluffy, roundish, almost flat as it opens.

*Number of florets.*—Variable, range from 10–21, average 12–15.

*Lasting quality.*—Average, blooms remain 5–11 days. Very self-fertile, better blooming if seed not allowed to mature.

Bud:

*Sepals.*—Narrow, pointed.

*Color.*—Turkey Red(721/1)(The Royal Horticultural Society Horticultural Colour Chart).

*Form.*—Pointed.

Florets:

*Size.*—½–1 inch across.

*Petalage.*—Double, 12–15 petals.

*Color.*—Delft Rose(020)(The Royal Horticultural Society Horticultural Colour Chart).

Texture: Ruffled and soft.

Form: Double flower, narrow petals range from ¼″ to ⅓″ wide.

Behavior: When blooming, this plant has many small, orange, fluffy looking blossoms that glow against foliage of small, dark green, notched, almost waxy leaves.

Having thus disclosed my invention, I claim:

1. A new and distinct variety of geranium plant, substantially as shown and described, characterized by its cascading growth habit; its distinctive small, orange, fluffy looking flowers; its continuous blooming habit; its unique dark green, small, notched foliage; and its exceptional heat tolerance.

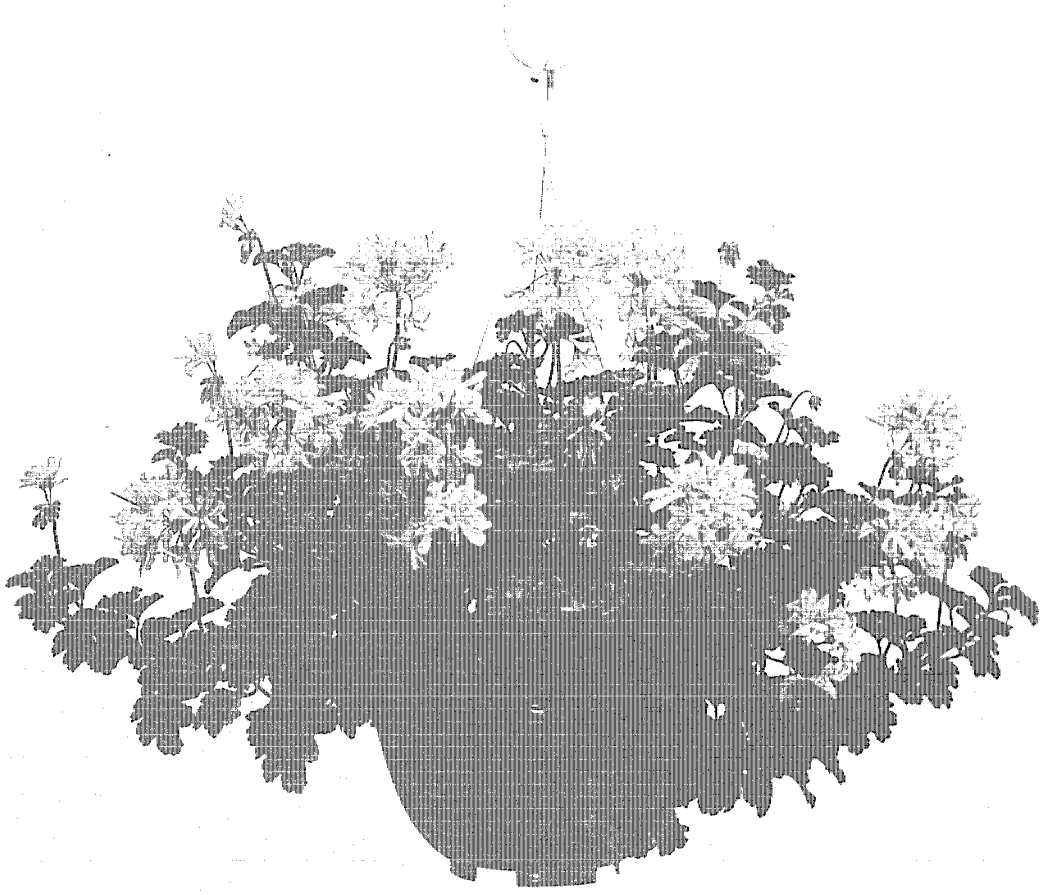

* * * * *